(12) United States Patent
Hegendoerfer et al.

(10) Patent No.: US 10,810,390 B2
(45) Date of Patent: Oct. 20, 2020

(54) TRANSMITTING A DATA RECORD (71) Applicant: Siemens Healthcare GmbH, Erlangen (DE)

(72) Inventors: Friedrich Hegendoerfer, Weilersbach (DE); Martin Korinth, Zorneding (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 0 days.

(21) Appl. No.: 16/482,036

(22) PCT Filed: Jan. 12, 2018

(86) PCT No.: PCT/EP2018/050714
§ 371 (c)(1),
(2) Date: Jul. 30, 2019

(87) PCT Pub. No.: WO2018/141528
PCT Pub. Date: Aug. 9, 2018

(65) Prior Publication Data
US 2019/0392187 A1    Dec. 26, 2019

(30) Foreign Application Priority Data
Feb. 6, 2017   (EP) .................................... 17154830

(51) Int. Cl.
*G06K 7/14*   (2006.01)
*G06K 7/10*   (2006.01)

(52) U.S. Cl.
CPC ....... *G06K 7/1417* (2013.01); *G06K 7/10722* (2013.01)

(58) Field of Classification Search
None
See application file for complete search history.

(56) References Cited

U.S. PATENT DOCUMENTS

2007/0181691 A1   8/2007   Chang
2012/0217293 A1   8/2012   Gratton

FOREIGN PATENT DOCUMENTS

DE    102013003044 A1 *  8/2014   ............. G06Q 10/20
DE    102013003044 A1    8/2014

OTHER PUBLICATIONS

Ishihara Takayuki et al: "Compatible 2D-Code Having Tamper Detection System with QR-Code", 2014 Tenth International Conference on Intelligent Information Hiding and Multimedia Signal Processing, 1 EEE, pp. 493-496, XP032715264, DOI: 10.1109/IIH-MSP.2014.129; 2014.

(Continued)

*Primary Examiner* — Kristy A Haupt
(74) *Attorney, Agent, or Firm* — Harness, Dickey & Pierce, P.L.C.

(57) ABSTRACT

The invention is based on a configuration change at a monitored device being detected by a first computer unit of a monitored device. Furthermore, a first data record is determined by means of the first computer unit of the monitored device, wherein the first data record comprises at least one item of public device information and an item of configuration information, and wherein the item of public device information is assignable one-to-one to the monitored device. Furthermore, an item of visual information based on the first data record is determined by means of the first computer unit of the monitored device. Furthermore, the item of visual information is transmitted optically from an output unit of the monitored device to an input unit of a mobile monitoring unit. Furthermore, a second data record is determined from the item of visual information by means of a second computer unit of the mobile monitoring unit, wherein from the second data record, at least the item of public device information and the item of configuration information are determinable. Furthermore, the second data (Continued)

record is transmitted from an interface of the mobile monitoring unit to a central data acquisition unit. Hereby the monitored device can be, in particular, a medical device, in particular, an imaging device, in particular, a mobile ultrasonic device or a mobile C-arm X-ray device.

20 Claims, 3 Drawing Sheets

(56) References Cited

OTHER PUBLICATIONS

Kuan-Chieh Liao et al: "A One-Time Password Scheme with QR-Code Based on Mobile Phone", INC, IMS and IDC, 2009 Fifth International Joint Conference on, IEEE, Piscataway, NJ, USA, Aug. 25, 2009 (Aug. 25, 2009), pp. 2069-2071, XP031564781, ISBN: 978-0- 7695-3769-6; 2009.
Partial European Search Report for European Patent Application No. 17154830 dated Jul. 20, 2017.
Extended European Search Report for European Patent Application No. 17154830 dated Oct. 11, 2017.
European Office Action for European Patent Application No. 17154830 dated Mar. 27, 2019.
International Search Report PCT/ISA/210 for International Application No. PCT/EP2018/050714 dated Apr. 18, 2018.
Written Opinion of the International Searching Authority PCT/ISA/237 for International Application No. PCT/EP2018/050714 dated Apr. 18, 2018.

\* cited by examiner

TRANSMITTING A DATA RECORD

PRIORITY STATEMENT

This application is the national phase under 35 U.S.C. § 371 of PCT International Application No. PCT/EP2018/050714 which has an International filing date of Jan. 12, 2018, which designated the United States of America and which claims priority to European patent application number EP17154830.8 filed Feb. 6, 2017, the entire contents of which are hereby incorporated herein by reference.

FIELD

Embodiments of the present application are directed to a system and method for transmitting a data record.

BACKGROUND

In many fields of technology, it is necessary to store information concerning a device installed at the customer centrally in a database at the manufacturer of the device or at a service provider. Such databases can, firstly, be necessary in order to meet regulatory requirements and, secondly, they can also be used to improve services that are provided. Of particular significance herein is storing the current configuration of the device comprising the installed physical components (the "hardware") and the control instructions (the "software") that are used, or the current condition or status of the device. However, such a configuration can change in the period of use of the device. In order always to store the current configuration of the device, the device must therefore be monitored.

Such devices to be monitored can be, in particular, medical technology systems, for example, ultrasonic devices or mobile X-ray devices, for which particularly strict regulatory requirements often apply.

It is possible, in particular for cost reasons, that the user of a device himself also carries out changes on instructions, for example, from the manufacturer, to the configuration of the device by hardware or software updates. The success or failure of these configuration changes must then be notified to the manufacturer of the device or a service provider. Information regarding changes of condition (e.g. the occurrence of an error condition) must also be sent to the manufacturer of the device or the service provider.

For this purpose, it is known to connect the monitored device to the Internet so that the monitored device can issue a feedback regarding the success or failure of the configuration change. Because of safety considerations, regulatory requirements, or for cost reasons, however, there are devices which are not connected to the Internet, for example, mobile ultrasonic devices. In the case of such, particularly mobile, devices, a feedback via the Internet is therefore not possible.

It is further known that users of the device communicate a feedback concerning the completed configuration change to the manufacturer of the device or the service provider, for example via telephone, fax or email and thereby provide the data of the configuration change manually and in a predetermined or freely selected format.

SUMMARY

The inventors have discovered that such a feedback is however, time-consuming and therefore entails costs. Furthermore, through transmission errors or intentional manipulation by the user, false information can be stored at the manufacturer of the device or at the service provider.

At least one embodiment of the present invention provides a rapid, economical and manipulation-proof method for transmitting the success of a configuration change at a central data acquisition unit.

Embodiments are directed to a method, a monitored device, a computer program product and a computer-readable storage medium.

Inventive achievements are described below, both in relation to the claimed devices and also in relation to the claimed method. Features, advantages or alternative embodiments mentioned herein are also transferable similarly to the other claimed subject matter and vice versa. In other words, the objective claims (which are directed, for example, to a device) can also be further developed with the features described or claimed in relation to a method. The corresponding functional features of the method are thereby provided by corresponding physical modules.

At least one embodiment of the invention is based on a configuration change in a monitored device being detected by a first computer unit of a monitored device. Furthermore, a first data record is determined via the first computer unit of the monitored device, wherein the first data record comprises at least one item of public device information and an item of configuration information, and wherein the item of public device information is assignable unambiguously to the monitored device. Furthermore, an item of visual information based on the first data record is determined via the first computer unit of the monitored device. Furthermore, the item of visual information is transmitted optically from an output unit of the monitored device to an input unit of a mobile monitoring unit. Furthermore, a second data record is determined from the item of visual information via a second computer unit of the mobile monitoring unit, wherein from the second data record, at least the item of public device information and the item of configuration information are determinable. Furthermore, the second data record is transmitted from an interface of the mobile monitoring unit to a central data acquisition unit. Hereby the monitored device can be, in particular a medical device, in particular an imaging device, in particular a mobile ultrasonic device or a mobile C-arm X-ray device.

At least one embodiment of the invention is directed to a method for transmitting a data record, comprising:

detecting a configuration change at a monitored device via a first processor of the monitored device;

firstly determining a first data record via the first processor of the monitored device, wherein the first data record includes at least one item of public device information and an item of configuration information and wherein the item of public device information is uniquely assignable to the monitored device;

secondly determining an item of visual information based upon the first data record, via the first processor of the monitored device;

firstly optically transmitting the item of visual information from an output unit of the monitored device to an input unit of a mobile monitoring unit;

thirdly determining a second data record from the item of visual information via a second processor of the mobile monitoring unit, wherein from the second data record, at least the item of public device information and the item of configuration information are determinable; and secondly transmitting the second data record from an interface of the mobile monitoring unit to a central data acquisition unit.

At least one embodiment of the invention further relates to a monitored device, configured to transmit a data record, comprising the following units:
- a first computer unit,
  - configured for detecting a configuration change at the monitored device,
  - further configured for a first determination of a first data record, wherein the first data record comprises at least one item of public device information and an item of configuration information, and wherein the item of public device information is assignable one-to-one to the monitored device,
  - further configured for second determination of an item of visual information based on the first data record, and
- an output unit configured for optical first transmission of the item of visual information to an input unit of a mobile monitoring unit.

At least one embodiment of the invention is directed to monitored device, configured to transmit a data record, comprising:
- a first processor, configured to
- detect a configuration change at the monitored device
- firstly determine a first data record, wherein the first data record includes at least one item of public device information and an item of configuration information, and wherein the item of public device information is assignable one-to-one to the monitored device,
- secondly determine an item of visual information based on the first data record; and an output unit configured to
- firstly optically transmit the item of visual information to an input unit of a mobile monitoring unit.

At least one embodiment of the invention is directed to a non-transitory computer program product storing a computer program, directly loadable into a memory store of a monitored device, including program portions to carry out the method of an embodiment upon the program portions being executed by the monitored device.

At least one embodiment of the invention is directed to a non-transitory computer-readable storage medium storing program steps, executable by a monitored device, to carry out the method of an embodiment upon the program portions being executed by the monitored device.

At least one embodiment of the invention can further also relate to a data transmission system, configured to transmit a data record, comprising the following devices:
a) a monitored device, comprising the following units:
a first computer unit,
  configured for detecting a configuration change at the monitored device,
  further configured for a first determination of a first data record, wherein the first data record comprises at least one item of public device information and an item of configuration information, and wherein the item of public device information is assignable one-to-one to the monitored device,
  further configured for second determination of an item of visual information based on the first data record,
an output unit, configured for optical first transmission of the item of visual information to an input unit of a mobile monitoring unit,
b) a mobile monitoring unit, comprising the following units:
an input unit, configured for the optical first reception of the item of visual information from the output unit of the monitored device,
a second computer unit, configured for a third determination of a second data record from the item of visual information via a second computer unit of the mobile monitoring unit,
wherein from the second data record, at least the item of public device information and the item of configuration information are determinable,
an interface, configured for second transmission of the second data record to a central data acquisition unit.

DETAILED DESCRIPTION OF THE EXAMPLE EMBODIMENT

At least one embodiment of the invention is based on a configuration change in a monitored device being detected by a first computer unit of a monitored device. Furthermore, a first data record is determined via the first computer unit of the monitored device, wherein the first data record comprises at least one item of public device information and an item of configuration information, and wherein the item of public device information is assignable unambiguously to the monitored device. Furthermore, an item of visual information based on the first data record is determined via the first computer unit of the monitored device. Furthermore, the item of visual information is transmitted optically from an output unit of the monitored device to an input unit of a mobile monitoring unit. Furthermore, a second data record is determined from the item of visual information via a second computer unit of the mobile monitoring unit, wherein from the second data record, at least the item of public device information and the item of configuration information are determinable. Furthermore, the second data record is transmitted from an interface of the mobile monitoring unit to a central data acquisition unit. Hereby the monitored device can be, in particular a medical device, in particular an imaging device, in particular a mobile ultrasonic device or a mobile C-arm X-ray device.

The inventors have recognized that through the transmission of the item of public device information and the item of configuration information to a mobile monitoring unit, a connection of the mobile monitoring unit to the central data acquisition unit, for example via the Internet, can be used. Therefore, the monitored device does not have to be directly connected to the central data acquisition unit and this leads to a cost saving and improved security of the monitored device.

Furthermore, due to the use of an optical transmission, it is not necessary to create a continuous connection, for example, a cable-bound connection or a radio connection, between the monitored device and the mobile monitoring unit. The mobile monitoring unit can therefore be used, firstly, in particular, for monitoring a plurality of monitored devices, and this represents a cost saving. Through the use of the optical transmission, the monitored device can furthermore not be manipulated by a third party, since no information and, in particular, no harmful code can be transmitted to the monitored device. Because of the optical transmission, it is further not necessary to acquire or pass on the item of public device information and the item of configuration information manually, so that the data record can be transmitted particularly rapidly and efficiently to the central data acquisition unit, and furthermore, careless mistakes by the user during the acquisition of the data are prevented.

According to a further embodiment of the invention, the item of configuration information comprises at least one item of information concerning the success of the configuration change at the monitored device. The success of a configuration change results, in particular, if the configuration change has been successfully carried out. In particular, it is possible to represent the item of visual information only when the configuration change of the monitored device was successful. The inventors have recognized that with an item of configuration information of this type, a correct data record in the central data acquisition unit can be achieved particularly easily.

According to a further embodiment of the invention, the item of visual information is contained in an image, wherein on the optical first transmission, the image is displayed on the output unit of the monitored system and the image is acquired by the input unit of the mobile monitoring unit. An item of visual information is contained, in particular, in an image if it can be recreated or reconstructed from the image alone. An item of visual information is also contained in an image, in particular, if the item of visual information is contained in an encrypted or encoded form in the image. The inventors have recognized that the outputting of an image on the output unit of the monitored device and the acquisition of the image with the input unit of the mobile monitoring unit is particularly cost-effective and efficient, since the suitable output unit and the suitable input unit are usually already present and are configured for the display or acquisition of an image and therefore the method can be carried out without costly modification of the monitored device or the mobile monitoring unit.

According to a further embodiment of the invention, the image comprises image regions wherein an image region has either a first color or a second color and wherein the first color and the second color differ at least in their brightness and/or in their color tone. The first color and the second color can also differ, in particular, in their brightness. The inventors have recognized that with such image regions, an item of visual information can be transmitted particularly efficiently.

According to a further embodiment of the invention, the item of visual information is contained in the geometric arrangement of the image regions of the image. The inventors have recognized that this geometric arrangement can be recognized by the input unit of the mobile monitoring unit particularly well, rapidly and with particularly few errors.

According to a further embodiment of the invention, the image comprises a one-dimensional barcode or a two-dimensional barcode. A one-dimensional barcode can be, in particular, a linear barcode, while a two-dimensional barcode can be, in particular, a stacked linear barcode, a matrix code or a point code. A two-dimensional barcode can be, in particular, a "Quick Response Code" (QR code for short). A one-dimensional barcode or a two-dimensional barcode can comprise, in particular, redundant regions. The inventors have recognized that with a one-dimensional barcode or a two-dimensional barcode, information can be transmitted particularly efficiently. Furthermore, one-dimensional barcodes and two-dimensional barcodes comprise redundant regions, so that errors in the transmission can be prevented. At the same time, with the redundant regions, the optical transmission is also accelerated, since inaccuracies in the positioning and the image acquisition can be compensated for by the mobile monitoring unit via the error redundancy.

According to a further embodiment of the invention, the item of public device information comprises a first identification number of the monitored device. A first identification number can be, in particular, a serial number of the monitored device. An identification number can also comprise, in particular, characters that are not numeric, for example, letters and special characters. The inventors have recognized that with the use of a first identification number, the data transmitted to the central data acquisition unit can be particularly easily and therefore rapidly assigned to the monitored device.

According to a further embodiment of the invention, the configuration change comprises the installation and/or the removal of a hardware and/or software component, wherein the item of configuration information comprises a second identification number of the hardware and/or software component. The inventors have recognized that with such an item of configuration information, the changed configuration of the monitored device can be described particularly quickly and efficiently. In particular, given the existence of a plurality of equal-value hardware and/or software components, it can be detected which of these components is used in which of the monitored devices.

According to a further embodiment of the invention, the item of visual information is configured such that a change of the item of configuration information and of the item of public device information is detectable via the mobile monitoring unit and/or via the central data acquisition unit. The inventors have recognized that in this way, transmission errors or intentional manipulation of the data is precluded. By this means, the item of configuration information can be stored, in particular error-free, in the central data acquisition unit.

According to a further embodiment of the invention, the item of visual information comprises at least the result of the use of a one-way hash function on the first data record. A technical expression for one-way hash function is "hash function". The inventors have recognized that through the use of a one-way hash function, the change of the item of configuration information and of the item of public device information can be detected particularly rapidly, and furthermore, the result of the use of a typical one-way hash function is short and is therefore quick and economical to transmit.

According to a further embodiment of the invention, the first data record further comprises an item of secret device information, wherein the item of secret device information is assignable one-to-one to the monitored device and wherein the item of secret device information is not determinable from the item of visual information. The inventors have recognized that by the use of an item of secret device information, a manipulation of the transmitted data can be precluded.

According to a further embodiment of the invention, the item of secret device information is stored both in the central data acquisition unit and also in the monitored device. The inventors have recognized that by such storage, a manipulation can be precluded particularly easily and cost-effectively.

According to a further possible embodiment of the invention, the configuration change comprises the installation and/or removal of a hardware and/or software component, and furthermore, the item of secret device information is stored both in the central data acquisition unit and also in the hardware and/or software component. The inventors have recognized that by such storage, the manipulation can be precluded particularly easily since for different configuration changes, in each case different items of secret device information can be selected.

According to a further embodiment of the invention, the second identification number of the monitored device is uniquely assignable, the second identification number being stored both in the central data acquisition unit and also in the new hardware and/or software component, and wherein the second identification number is not determinable from the item of visual information. The inventors have recognized that with such a second identification number, manipulation security can be guaranteed without storing additional information in the monitored device.

According to a further embodiment of the invention, the second data record is a query part of a uniform resource locator, wherein the second transmission comprises the invoking of the uniform resource locator (URL). The query part of a URL is designated the "Query". A uniform resource locator can be, in particular, an electronic reference. The technical expression for an electronic reference is "Hyperlink". The second transmission can then be carried out through the invoking of the hyperlink, wherein the query part is transmitted to the target of the invocation. The inventors have recognized that by use of a uniform resource locator, existing communication infrastructure can be used. This communication infrastructure can be, for example, the Internet. It is therefore not necessary to construct and/or keep in reserve a costly individual communication infrastructure.

At least one embodiment of the invention further relates to a monitored device, configured to transmit a data record, comprising the following units:
  a first computer unit,
    configured for detecting a configuration change at the monitored device,
    further configured for a first determination of a first data record, wherein the first data record comprises at least one item of public device information and an item of configuration information, and wherein the item of public device information is assignable one-to-one to the monitored device,
    further configured for second determination of an item of visual information based on the first data record, and
  an output unit configured for optical first transmission of the item of visual information to an input unit of a mobile monitoring unit.

Such a monitored device can be configured, in particular, to carry out at least one embodiment of the inventive method and its embodiments described above. The monitored device is configured to carry out this method and its embodiments in that the first computer unit and the output unit are configured to carry out the corresponding method steps.

At least one embodiment of the invention can further also relate to a data transmission system, configured to transmit a data record, comprising the following devices:
  a) a monitored device, comprising the following units:
    a first computer unit,
      configured for detecting a configuration change at the monitored device,
      further configured for a first determination of a first data record, wherein the first data record comprises at least one item of public device information and an item of configuration information, and wherein the item of public device information is assignable one-to-one to the monitored device,
      further configured for second determination of an item of visual information based on the first data record,
    an output unit, configured for optical first transmission of the item of visual information to an input unit of a mobile monitoring unit,
  b) a mobile monitoring unit, comprising the following units:
    an input unit, configured for the optical first reception of the item of visual information from the output unit of the monitored device,
    a second computer unit, configured for a third determination of a second data record from the item of visual information via a second computer unit of the mobile monitoring unit,
    wherein from the second data record, at least the item of public device information and the item of configuration information are determinable,
    an interface, configured for second transmission of the second data record to a central data acquisition unit.

Such a data transmission system can be configured, in particular, to carry out at least one embodiment of the inventive method and its embodiments described above. The data transmission system is configured to carry out this method and its embodiments in that the monitored device and its associated units as well as the mobile monitoring unit and its associated units are configured to carry out the corresponding method steps.

At least one embodiment of the invention also relates to a computer program product having a computer program and a computer-readable medium for a monitored device or a data transmission system. A realization largely through software has the advantage that conventionally used monitored devices or data transmission systems can also easily be upgraded with a software update in order to operate in the manner according to at least one embodiment of the invention.

Such a computer program product can comprise, apart from the computer program, additional components, if relevant, for example, documentation and/or additional components including hardware components, for example, hardware keys (dongles, etc.) in order to use the software.

At least one embodiment of the invention can also relate to a computer program product having a computer program which is directly loadable into a memory store of a data transmission system, having program portions in order to carry out all the steps of at least one embodiment of the method when the program portions are executed by the data transmission system.

At least one embodiment of the invention can also relate to a computer-readable storage medium on which program portions that are executable by a data transmission system are stored, in order to carry out all the steps of the method of at least one embodiment when the program portions are executed by the data transmission system.

A monitored device can be, in particular, a technical medical device, in particular a medical imaging device. A monitored device can, in particular, be configured to be mobile, so that it can be used in different premises.

The condition or the status of the monitored device can, in particular, be described as the configuration. The condition of the monitored device also comprises, in particular, the hardware components included or the installed software components. An item of configuration information is an item of information concerning the current configuration of the monitored device or an item of information concerning a change in the configuration of the monitored device. A change in the configuration is, in particular, a change in the installed software components or a change in the included hardware components, or a change in the current status of the monitored device.

An item of visual information is, in particular, an item of information contained in a medium such that the item of visual information can be transmitted via electromagnetic radiation in the visible spectrum, wherein the electromagnetic radiation has a wavelength, in particular, of between 200 nm and 800 nm, in particular a wavelength of between 380 nm and 640 nm. An item of visual information can, in particular, also be empty. The item of visual information can, in particular, also be identical to the second data record. Furthermore, the item of visual information comprises, in particular, at least indirectly the item of public device information and the item of configuration information, in particular, the item of visual information can comprise the item of public device information and the item of configuration information.

The brightness of a color can denote, in particular, the photometric brightness of the color. A first color and a second color can each be, in particular, a gray tone. A gray tone is provided, for example, in the reg-green-blue (RGB) model in that all three color components have the same value. The first color can be given, in particular, in that in the RGB model, all the color components have a value of under 50% of the maximum value, in particular under 10% of the maximum value, in particular under 1% of the maximum value, and the first color can therefore, in particular, also be black. The second color can be given, in particular, in that in the RGB model, all the color components have a value of over 50% of the maximum value, in particular over 90% of the maximum value, in particular over 99% of the maximum value, and the second color can therefore, in particular, also be white. Hereby, the maximum value denotes the maximum value of a color component.

A one-way hash function thereby maps input values onto output values such that it is possible with, at most, a great computation effort to find, for a given output value, an associated input value which is mapped by the one-way hash function onto the given output value. By this, a one-way hash function can be used to transmit data in a forgery-proof manner.

A one-way hash function can be in particular a weakly collision resistant one-way hash function. For a weakly collision resistant one-way hash function, it is possible with, at most, a great computation effort to find for a given first input value, a second input value different from the first input value, so that the given first input value and the second input value are represented on the same output value. A one-way hash function can be, in particular, a strongly collision resistant one-way hash function. For a strongly collision resistant one-way hash function, it is possible with, at most, a great computation effort to find a first input value, a second input value different from the first input value, so that the given first input value and the second input value are represented on the same output value. Hereby, the finding of a value with, in particular, at most a great computation effort is possible if no algorithm to be used for determining the value exists and the value can only be found by systematic testing of possible solutions (a technical term for this being "brute force"), in particular if the systematic testing cannot be carried out by a single known state-of-the-art processor in less than one year.

A uniform resource identifier (URI) is defined in the standard RFC 3986 and includes a string of characters to identify resources, in particular web sites, files and web services. Apart from stating the site of a resource, a URI can also contain a query part (query). A uniform resource locator (URL) is a URI which has additional information for finding the resource by specifying the primary access mechanism. A synonym for URI is "hyperlink" or "link".

Figure 1:
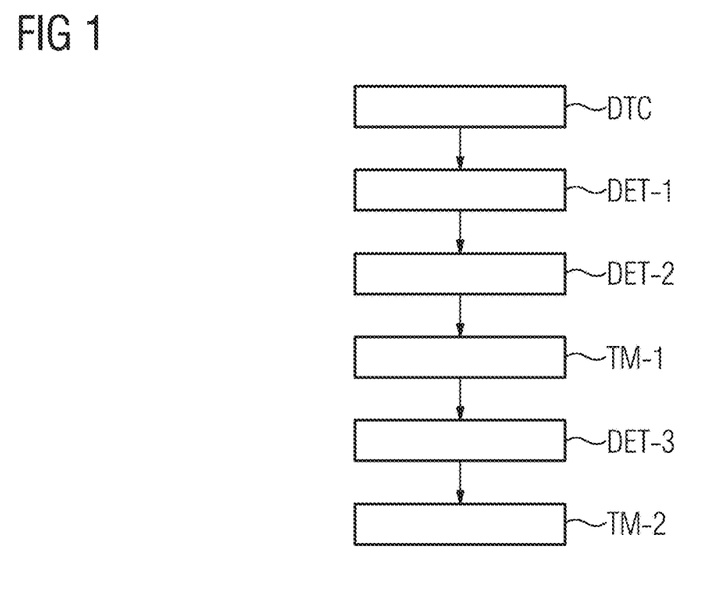
FIG. 1 shows a flow diagram of an example embodiment of the method.

FIG. 1 shows a flow diagram of a first, a second and a third example embodiment of the inventive method.

In the first example embodiment, the monitored device 200 is a mobile medical technical device, in particular a mobile ultrasonic device which is not connected to the Internet. A new software version which is to be made available to the user via a storage medium is to be installed by the user on this ultrasonic device and the success of the software installation is then to be notified to a central site. It is also conceivable in this case that individual software components (for example apps or special protocols) are installed and/or removed.

In the second example embodiment, the monitored device 200 is a mobile X-ray device, the X-ray tube of which is exchanged by the user. In this case, for example, an identification number of the newly installed X-ray tube is communicated to the manufacturer so that it can create a unique association between the X-ray devices and the installed X-ray tubes.

In the third example embodiment, due to an error, the mobile X-ray device changes over from the operational state into an error state or vice versa and this information is to be communicated to the manufacturer.

Alternatively, the monitored device 200 can be other devices, for example, a computed tomography device, a magnetic resonance tomography unit, a positron emission tomography unit, a laboratory diagnostic device or a robot.

The first step in the example embodiments disclosed is the detection DTC of a configuration change of a monitored device 200 via a first computer unit 202 of the monitored device 202.

In the first example embodiment, the detection DTC takes place via a signal which is transmitted at the software installation by an installation program to the computer unit 202. Alternatively, the detection DTC can also be carried out by a computer program which is continually executed on the computer unit 202 of the monitored device 200 and can detect changes to the version number of the software executed on the monitored device and further, this computer program can establish the addition or removal of software components.

In the second and third example embodiment, the detection DTC is also carried out by a computer program which is continually executed on the computer unit 202 of the monitored device 200 and monitors the current hardware configuration and/or the current condition of the monitored device 200. In the first example embodiment, this computer program can, in particular, store a target list of the hardware constituents installed in the monitored device 200 with the associated identification number and can compare this list with the actual identification numbers of the installed hardware parts. Furthermore, this computer program can detect changes to the version number of the software executed on the monitored device 200 and furthermore, this computer program can detect the addition or removal of software components. Furthermore, this computer program can monitor the condition of the monitored device 200, in particular error messages.

The next step in the example embodiments shown is the first determination DET-1 of a first data record 400 via the first computer unit 202 of the monitored device 200, wherein the first data record 400 comprises at least one item of public device information 401 and an item of configuration information 402, and wherein the item of public device information 401 is assignable uniquely to the monitored device 200. In the example embodiments shown, the item of public device information 401 is the serial number of the monitored device 200. The serial number of the monitored device 200 is uniquely assigned to the monitored device 200 such that a monitored device 200 is assigned exactly one serial number and that a serial number is assigned to only exactly one monitored device 200.

In the first example embodiment shown, the item of configuration information 402 is the version number of the software version that is installed at the configuration change on the monitored device. If, alternatively a software component is added or removed, the item of configuration information 402 concerns an identification number of the added or removed software component, for example a hash value of the executable installation or deinstallation routine. In the second example embodiment, the item of configuration information 402 is an identification number of the new X-ray tube, in particular a serial number of the new X-ray tube. This configuration information 402 can be stored, for example, on a readable storage unit in the X-ray tube. In the third example embodiment, the item of configuration information 402 comprises the prior condition of the monitored device 200, the new condition of the monitored device 200 and an item of time information, the time information giving the time point of the condition changes.

In the first example embodiment, the first data record 400 further comprises the result 403 of the use of a one-way hash function on a combination of the item of public device information 401, the item of configuration information 402 and an item of secret device information 404. The one-way hash function is here designated a hash function and the result 403 of the application of the hash function is designated a hash value 403. Hereby, the item of secret device information 404 is only stored on the monitored device 200 and in the central data acquisition unit 240. The item of secret device information 404, however, is not determinable by the mobile monitoring unit 220. By this means, it is not possible for the user of the mobile monitoring unit 220 to calculate the hash value 403 from the item of public device information 401 and the item of configuration information 402.

In this first example embodiment, the hash function represents exactly one input value to an associated hash value 403. In order to use the hash function on the item of public device information 401, the item of configuration information 402 and the item of secret device information 404, in the example embodiment shown, the hash function is applied to a linking of a character chain corresponding to the item of public device information 401, a character string corresponding to the item of configuration information 402 and a character string corresponding to the item of secret device information 404. A character string corresponds in particular to an item of information when the information content of the character string and the information are identical. A linking of character strings can take place, in particular, through the creation of a new character string, so that the linked character strings are partial character strings of the new character string. If the item of public device information 401, the item of configuration information 402 or the item of secret device information 404 are numbers, an associated character string is, in particular, the digit sequence which represents the number in the decimal system, in the hexadecimal system or the binary system. Alternatively, for linking character strings, in particular, from a plurality of information items, exactly one input value for the hash function can be created in that the plurality of information items can be converted by an arithmetic operation or a character string operation into a new item of information.

In the first example embodiment described, as the hash function, the SHA-1 (Secure Hash Algorithm 1) hash function, which is specified in RFC 3174, is used. It is also possible to use other hash functions. Known hash functions are MD5 (Message Digest Algorithm 5), SHA-2 (in particular SHA-224, SHA-256, SHA-384, SHA-512, SHA-512/224, SHA-512/256) and SHA-3 (in particular SHA3-224, SHA3-256, SHA3-384, SHA3-512, SHAKE128 and HAKE256). Also known are the hash functions BLAKE, Grøstl, JH and Skein. It is naturally also possible to use hash functions other than those mentioned here. The selection of the actual hash function is unimportant for the sequence of embodiments of the inventive method.

The next step of the example embodiments described is the second determination DET-2 of an item of visual information 420 on the basis of the first data record 400 via the first computer unit 202 of the monitored device 200. In the first example embodiment, the item of visual information 420 involves a link which contains the first data record 400. The first data record 400 is thereby the query part of the link. The item of visual information 420 in the form of the link is encoded in a QR code 500. Alternatively, other one-dimensional or two-dimensional barcodes can also be used. Examples of two-dimensional barcodes are matrix barcodes such as an Aztec Code (according to the ISO/IEC 24778 standard) or a Data Matrix (according to the ISO/IEC 16022 standard), and stacked barcodes such as a PDF417 code (according to the ISO/IEC 15438 standard).

In the second and the third example embodiment, what is involved in the item of visual information 420 is data in a format that can be read out by the mobile monitoring unit 220 and which is encoded in a linear barcode 600. Known formats that can be read out are, in particular, XML and JSON. Known linear barcodes 600 are EAN codes (according to the ISO/IEC 15420 standard) or "Code 128" (according to the ISO/IEC 15417 standard). A linear barcode 600 is a subform of a one-dimensional barcode.

It is also possible to use other one-dimensional or two-dimensional barcodes. In particular it is also possible to use non-standardized barcodes. The type of the barcodes used is not dependent upon the type of the monitored device 200 or on the contents of the first data record 400 or the item of visual information 420, but only on the technical possibilities of the output unit 204 and the input unit 224. Furthermore, the sequence of the inventive method is dependent upon the type of barcode used.

Alternatively to the example embodiments described, it is also possible that the item of visual information 420 is a character string which is displayed on an output unit 204 of the monitored device 200. The user can acquire this character string via an input unit 224 of the mobile monitoring unit, in particular via a keyboard or a screen keyboard.

Alternatively to the example embodiments described, it is also possible that, dependent upon the item of configuration information 402, the item of visual information 420 is empty and that no visual information 420 is displayed on the output unit 204 of the monitored device 200. This can be the case, in particular, if the configuration change in the form of an installation, a removal or a change in the hardware or software of the monitored device 200 was not successful. If no visual information 420 is displayed, then no second data record can be passed on to the central data acquisition unit 240 and no success of the configuration change can be assigned to the monitored device 200 in the central data acquisition unit 240. Typically, in such an alternative, a failure of the configuration change is stored as standard in the central data acquisition unit 240 of the monitored device 200, wherein the stored value is changed only in the event of a success notification. The further steps of the method are then carried out in this example embodiment only in the event of a success of the configuration change.

The next step of the example embodiments described is the optical first transmission TM-1 of the item of visual information 420 from an output unit 204 of the monitored device 200 to an input unit 224 of a mobile monitoring unit 220. The optical first transmission TM-1 takes place here in that the QR code 500 or the linear barcode 600 is displayed on the output unit 204 of the monitored device, wherein the QR code 500 or the linear barcode 600 encode the item of visual information 420. The output unit 204 is hereby a screen. Alternatively, the output unit 204 can also be a printer which prints out the QR code 500 or the linear barcode 600 onto paper. The input unit 224 of the mobile monitoring unit is hereby a camera. This camera is configured to record an image of a QR code 500 or of the linear barcode 600. The optical first transmission TM-1 takes place hereby in that the camera of the mobile monitoring unit makes an image of the output unit 204, here in particular of the screen, of the monitored device 200. Alternatively, the input unit 224 can also be a scanner unit. Furthermore, the input unit 224 can also be a keyboard with which a user can input into the mobile monitoring unit the information represented on the output unit 204.

As the next step of the example embodiments described, the third determination DET-3 of a second data record from the item of visual information 420 takes place via a second computer unit 222 of the mobile monitoring unit 220, wherein from the second data record, at least the item of public device information 401 and the item of configuration information 402 are determinable. In the example embodiments described, via the second computer unit 222, the QR code 500 or the linear barcode 600 is recognized, the item of visual information 420 is extracted and is converted into a second data record, wherein the second data record comprises a format that is readable by the central data acquisition unit 220. The item of visual information 420 can, in particular, be identical to the second data record.

The last step of the example embodiments described is the second transmission TM-2 of the second data record from an interface 221 of the mobile monitoring unit 220 to a central data acquisition unit 240. In the first example embodiment described, the second transmission TM-2 takes place such that the link contained in the QR code 500 is invoked. The address part of the link refers hereby to the central data acquisition unit 240 and through the invoking of the link, the information contained in the query part is passed on via the Internet 230 to the central data acquisition unit 240. The central data acquisition unit can then, on the basis of the item of secret device information 404 also stored in it, verify the second data record. Subsequently, it can store the item of configuration information 402 in the data record belonging to the monitored device in that it assigns the item of public device information to the monitored device 200. In the second and the third example embodiments, the application communicates on the mobile monitoring unit 220 via a previously defined protocol with the central monitoring unit, for example in that an email with a previously defined formatting is sent. A central data acquisition unit 240 can be, in particular, a database or a database server or, alternatively, the central data acquisition unit 240 can also be a web server or an email server.

Figure 2:
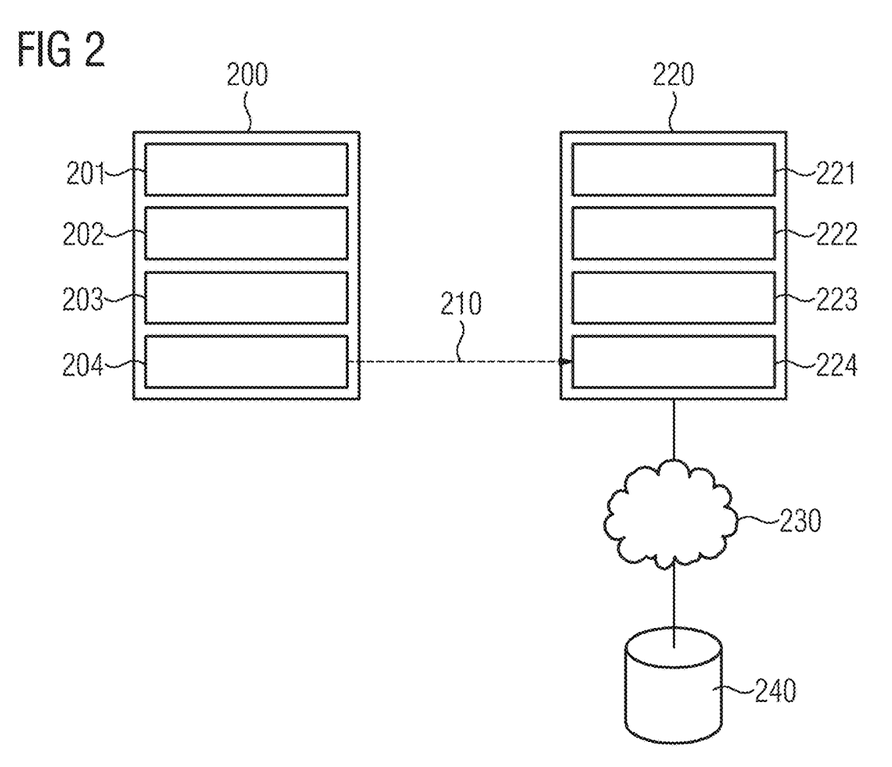
FIG. 2 shows a monitored device together with a mobile monitoring unit and a central data acquisition unit.

FIG. 2 shows a monitored device 200 together with a mobile monitoring unit 220 and a central data acquisition unit 240. The monitored device hereby comprises an interface 201, a first computer unit 202, a first storage unit 203 and an output unit 204. The mobile monitoring unit 220 comprises an interface 221, a second computer unit 222, a second storage unit 223 and an input unit 224. The output unit 204 of the monitored device 200 is connected to the input unit 224 of the mobile monitoring unit 220 via an optical channel 210. Furthermore, the mobile monitoring unit 220 is connected via a network 230 to the central data acquisition unit 240. The monitored device 200 can comprise, in particular, a computer, a microcontroller or an integrated circuit which comprises the interface 201, the first computer unit 202, the first storage unit 203 and/or the first output unit 204. A mobile monitoring unit 220 can also be, in particular, a computer, a microcontroller or an integrated circuit. A mobile monitoring unit 220 can also be, in particular, a mobile telephone, in particular, a Smartphone. An interface 201, 221 can be a hardware or software interface (for example, PCI bus, USB or Firewire). A first computer unit 202 and a second computer unit 222 can comprise hardware elements or software elements, for example, a microprocessor or an FPGA (Field Programmable Gate Array). A first storage unit 203 and a second storage unit 223 can be realized as a non-permanent working memory (Random Access Memory, RAM) or as a permanent mass storage unit (hard disk, USB stick, SD card, solid state disk). An output unit 204 can be, in particular, a screen or alternatively, it can be a printer. An input unit 224 is, in particular, a camera. However, it can also be a keyboard, a mouse or a scanner. A network 230 can be an Intranet or, in particular, the Internet. A central data acquisition unit for 240 can be realized, in particular, via a database and the central data acquisition unit 240 can further comprise a computer unit for data administration.

The input unit 224 of the mobile monitoring unit 220 is configured to acquire the item of visual information 420 displayed by the output unit 204 of the monitored device 200. The item of visual information 420 is thereby transmitted via an optical medium 210, wherein the optical medium is the ambient air in this case. Hereby, the item of visual information 420 can be displayed or encoded, in particular, via an image, in particular, via a QR code 500 or a linear barcode 600. In the example embodiment described, if the output unit 204 is, for example, a screen, then the input unit 224 can be configured as a camera which can record a QR code 500 displayed on the screen. If the output unit 204 is a printer which prints paper with the item of visual information 420, the input unit 224 can also be a camera or a scanner.

Figure 3:
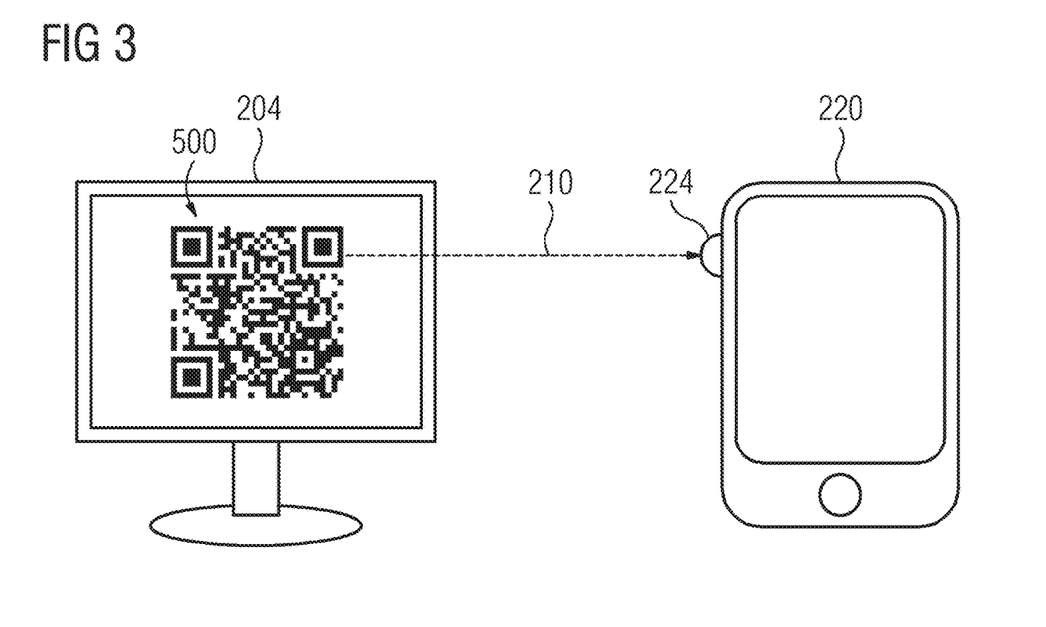
FIG. 3 shows an output unit of a monitored device and an input unit of a mobile monitoring unit.

FIG. 3 shows an output unit 204 of a monitored device 200 and an input unit 224 of a mobile monitoring unit 220 in the first example embodiment. The output unit 204 is herein a screen or a monitor of the mobile ultrasonic unit which is configured to display a QR code 500. The mobile monitoring unit 220 is configured in this example embodiment as a mobile telephone, in particular, as a Smartphone and its input unit 224 as a camera, in particular a photographic camera which is configured to acquire a QR code 500. The optical transmission medium 210 is hereby provided by the ambient air. The mobile telephone can communicate via a mobile radio network or via a wireless network (e.g. WLAN) with the network 230 (here the Internet) and thus with the central data acquisition unit 240.

Figure 4:
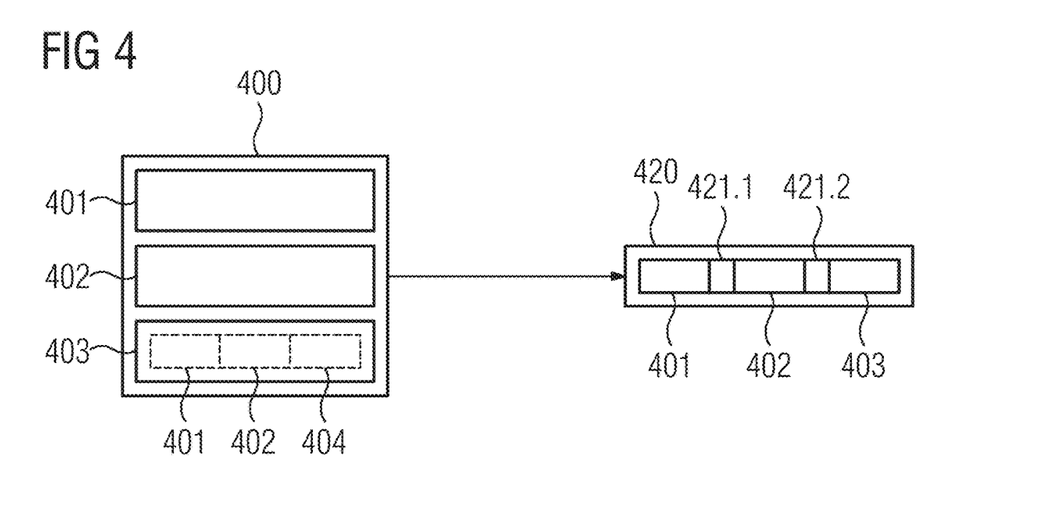
FIG. 4 shows a first data record with an associated item of visual information.

FIG. 4 shows the first data record 400 and an associated item of visual information 420 in the first example embodiment. The first data record 400 comprises an item of public device information 401, an item of configuration information 402 and a hash value 403. The hash value 403 has been determined by the use of a hash function, the hash function having been used on a combination of the item of public device information 401, the item of configuration information 402 and an item of secret device information 404. In the example embodiment shown, the item of public device information 401 is a serial number and the item of configuration information 402 is a software version number, while the item of secret device information 404 is a secret serial number. The combination of the item of public device information 401, the item of configuration information 402 and the item of secret device information 404 takes place in that the information items are converted into a character string and that the character strings are linked. The hash function is then used on the linked character string. The item of visual information 420 also comprises the item of public device information 401, the item of configuration information 402 and the hash value 403, as well as separators 421.1, 421.2. These information items are linked behind one another as character strings. The character string thereby formed can optionally be encoded as a QR code 500 or as a linear barcode 600, although other codings are also possible.

In the example embodiment described, for example, a hyperlink in the following form can be used:

http://example.com/verify.php?s=123&c=2&h=654

Hereby, "http" denotes the scheme used in the URL, "example.com" denotes the host of the URL which here corresponds to the address of the central data acquisition unit 240, "verify.php" is the path of the URL and "s=123&c=2&h=654" is the query part of the URL. In the query part, with "s=123", the item of public device information 401, with "c=2", the item of configuration information 402 and with "h=654", the hash value 404 are listed and the individual information items are separated by the ampersand "&" as the separator sign 421.1, 421.2. By invoking the link, the query part is sent to the central data acquisition unit 240.

Figure 5:
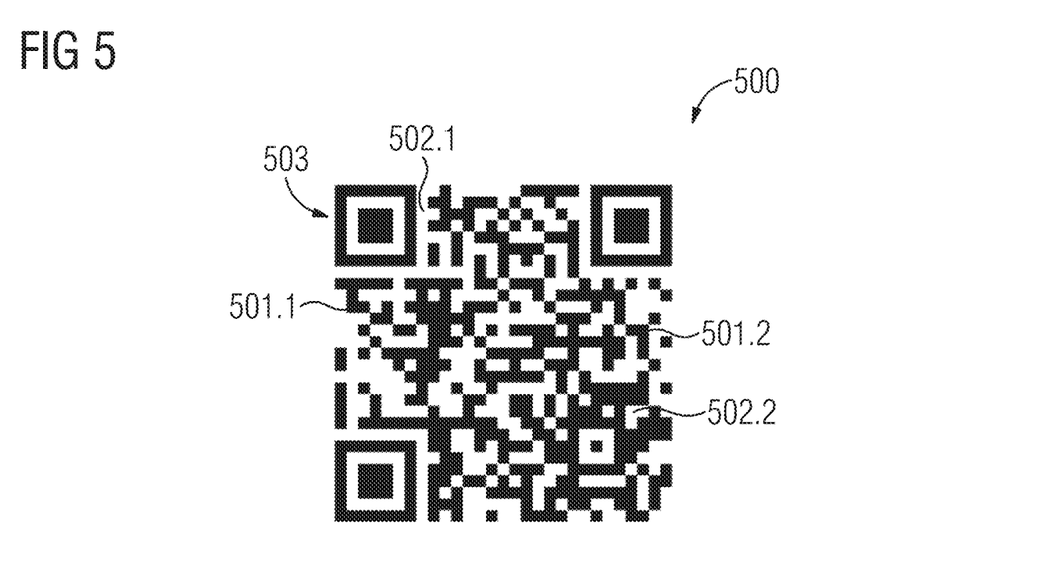
FIG. 5 shows a QR code.

FIG. 5 shows a QR code 500. The QR code 500 includes first regions 501.1, 501.2 in black and second regions 502.1, 502.2 in white. Thereby, the first regions 501.1, 501.2 are a collection of black pixels, while the second regions 502.1, 502.2 are a collection of white pixels. The pixels of the QR code 500 are arranged in a grid structure. The QR code 500 also comprises position marks 503 in the form of a geometric arrangement of white and black pixels, and a QR code can also contain further marks or patterns which facilitate an acquisition of the QR code 500 and/or a decoding of the QR code 500. The information of the QR code 500 is contained in the geometric form of the first regions 501.1, 501.2 and the second regions 502.1, 502.2. The geometrical form of the first regions 501.1, 501.2 and the second regions 502.1, 502.2 in this example embodiment is given by contiguous square pixels in a grid.

A QR code 500 can contain redundant information. This redundant information can be used, in particular, to compensate for errors in the representation or in the acquisition of QR codes 500. Thereby, different redundancy levels are possible, in particular, more than 7% redundant content, in particular, more than 15% redundant content, in particular, more than 25% redundant content, in particular, more than 30% redundant content. Hereby, a content of the QR code 500 is considered redundant if the item of visual information 420 contained in the QR code 500 can also be determined without this content. For the implementation of the error correction, in particular, the Reed-Solomon encoding is known.

Figure 6:
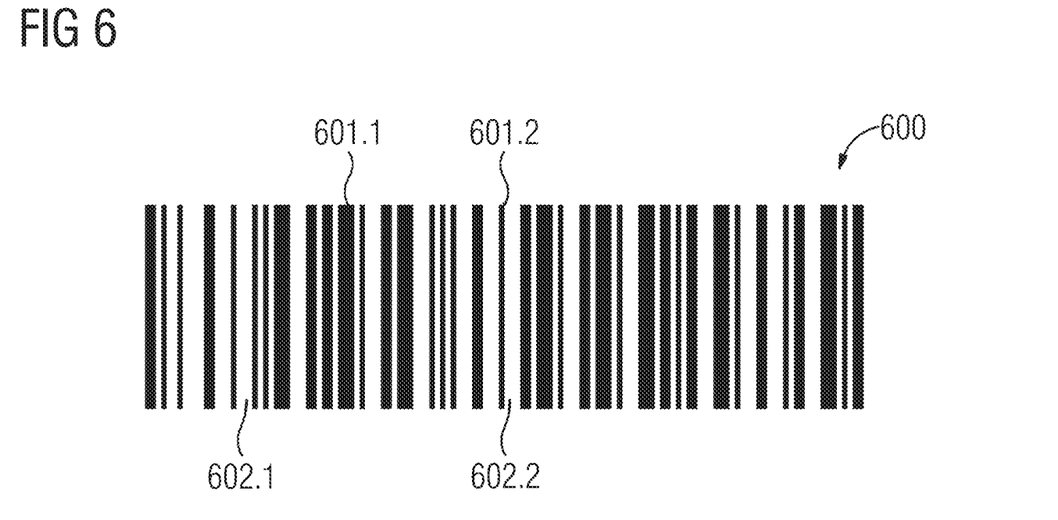
FIG. 6 shows a linear barcode.

FIG. 6 shows a linear barcode 600. The linear barcode includes black bars 601.1, 601.2 and white bars 602.1, 602.2. The information encoded in the linear barcode 600 is contained in the different thicknesses of the bars 601.1, 601.2, 602.1, 602.2. The linear barcode 600 can also contain redundant information, so that an error correction when acquiring the linear barcode 600 is possible. In particular, it is known to use check characters.

The invention claimed is:

1. A method for transmitting a data record, comprising:
   detecting a configuration change at a monitored device via a first processor of the monitored device;
   firstly determining a first data record via the first processor of the monitored device, wherein the first data record includes an item of public device information and an item of configuration information and wherein the item of public device information is uniquely assignable to the monitored device;
   secondly determining an item of visual information based upon the first data record, via the first processor of the monitored device;
   firstly optically transmitting the item of visual information from an output unit of the monitored device to an input unit of a mobile monitoring unit;
   thirdly determining a second data record from the item of visual information via a second processor of the mobile monitoring unit, wherein from the second data record, at least the item of public device information and the item of configuration information are determinable; and
   secondly transmitting the second data record from an interface of the mobile monitoring unit to a central data acquisition unit, wherein the item of configuration information includes at least one item of information concerning a success of the configuration change at the monitored device.

2. The method of claim 1, wherein the item of visual information is contained in an image, and wherein on the optical first transmission, the image is displayed on the output unit of the monitored device and the image is acquired by the input unit of the mobile monitoring unit.

3. The method of claim 2, wherein the image comprises at least one first image region and a second image region, wherein the at least one first image region has a first color and the at least one second image region has a second color and wherein the first color and the second color differ in at least one of brightness and color tone.

4. The method of claim 3, wherein the item of visual information is contained in the geometric arrangement of the at least one first image region and the at least one second image region of the image.

5. The method of claim 4, wherein the image comprises a one-dimensional barcode or a two-dimensional barcode.

6. The method of claim 1, wherein the item of public device information includes a first identification number of the monitored device.

7. The method of claim 1, wherein the configuration change includes at least one of the installation and the removal of at least one of a hardware and software component, and wherein the item of configuration information includes a second identification number of at least one of the hardware and software component.

8. The method of claim 1, wherein the item of visual information is configured such that a change of the item of configuration information and a change of the item of public device information is detectable via at least one of the mobile monitoring unit and via the central data acquisition unit.

9. The method of claim 8, wherein the item of visual information includes at least a result of a use of a one-way hash function on the first data record.

10. The method of claim 9, wherein the first data record further includes an item of secret device information, and wherein the item of secret device information is assignable one-to-one to the monitored device, and wherein the item of secret device information is not determinable by the mobile monitoring unit from the item of visual information.

11. The method of claim 1, wherein the second data record is a query part of a uniform resource locator, and wherein the second transmission includes invoking of the uniform resource locator.

12. A non-transitory computer program product storing a computer program, directly loadable into a memory store of a monitored device, including program portions to carry out the method of claim 1 upon the program portions being executed by the monitored device.

13. A non-transitory computer-readable storage medium storing program steps, executable by a monitored device, to carry out the method of claim 1 upon the program portions being executed by the monitored device.

14. The method of claim 1, wherein the item of visual information is contained in an image, and wherein on the optical first transmission, the image is displayed on the output unit of the monitored device and the image is acquired by the input unit of the mobile monitoring unit.

15. The method of claim 14, wherein the image comprises at least one first image region and a second image region, wherein the at least one first image region has a first color and the at least one second image region has a second color and wherein the first color and the second color differ in at least one of brightness and color tone.

16. The method of claim 15, wherein the item of visual information is contained in the geometric arrangement of the at least one first image region and the at least one second image region of the image.

17. The method of claim 16, wherein the image comprises a one-dimensional barcode or a two-dimensional barcode.

18. The method of claim 1, wherein the monitored device is a medical device.

19. A monitored device, configured to transmit a data record, comprising:
   a first processor, configured to
      detect a configuration change at the monitored device
      firstly determine a first data record, wherein the first data record includes at least one item of public device information and an item of configuration information, and wherein the item of public device information is assignable one-to-one to the monitored device,
      secondly determine an item of visual information based on the first data record; and
   an output unit configured to
      firstly optically transmit the item of visual information to an input unit of a mobile monitoring unit, wherein the item of configuration information includes at least one item of information concerning a success of the configuration change at the monitored device.

20. The monitored device of claim 19, wherein the monitored device is a medical device.

* * * * *